(12) United States Patent
Ou et al.

(10) Patent No.: US 7,040,805 B1
(45) Date of Patent: May 9, 2006

(54) METHOD OF INFRARED THERMOGRAPHY

(75) Inventors: Shichuan Ou, Beavercreek, OH (US); Srinath V. Ekkad, Baton Rouge, LA (US); Richard B. Rivir, Bellbrook, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 31 days.

(21) Appl. No.: 10/857,373

(22) Filed: May 24, 2004

(51) Int. Cl.
*G01N 25/72* (2006.01)
*G01K 17/10* (2006.01)

(52) U.S. Cl. .............................. 374/43; 374/29; 374/5; 702/135; 702/136; 250/341.6

(58) Field of Classification Search .................. 374/43, 374/29, 30, 5, 44; 702/134, 135, 136; 250/341.6
See application file for complete search history.

(56) References Cited

U.S. PATENT DOCUMENTS

| | | | | |
|---|---|---|---|---|
| 3,504,524 | A * | 4/1970 | Maley | 374/5 |
| 3,566,669 | A * | 3/1971 | Lawrence et al. | 374/5 |
| 4,420,965 | A * | 12/1983 | Farkas et al. | 374/43 |
| 4,885,633 | A * | 12/1989 | Buck | 374/162 |
| 4,902,139 | A * | 2/1990 | Adiutori | 374/137 |
| 5,111,046 | A | 5/1992 | Bantel | 250/330 |
| 5,131,758 | A * | 7/1992 | Heyman et al. | 374/5 |
| 6,422,743 | B1 * | 7/2002 | Nirmalan et al. | 374/43 |
| 6,517,236 | B1 | 2/2003 | Sun et al. | 374/4 |
| 6,517,238 | B1 * | 2/2003 | Sun et al. | 374/43 |
| 6,585,408 | B1 * | 7/2003 | El-Gabry et al. | 374/43 |
| 6,732,582 | B1 * | 5/2004 | Bunker et al. | 374/45 |
| 6,804,622 | B1 * | 10/2004 | Bunker et al. | 374/43 |

OTHER PUBLICATIONS

Dittmar-J; Schulz-A; Wittig-S."Assessment of various film-cooling configurations including shaped and compound angle holes based on large-scale experiments." Transactions-of-the-ASME-The-Journal-of-Turbomachinery (USA), vol. 125, No. 1, pp. 57-64 (Jan. 2003).*

Bizzak al. "Use of a laser-induced fluorescence thermal imaging system for local jet impingement heat transfer measurement." International-Journal-of-Heat-and-Mass-Transfer (UK), vol. 38, No. 2, pp. 267-274 (Jan. 1995).*

"Leading Edge Film Cooling Heat Transfer With High Free Stream Turbulence Using A Transient Liquid Crystal Image Method" by Ou et al., International Journal of Heat and Fluid Flow 22, 614-623, 2001 (no month).

"A Method For The Simultaneous Determination Of Local Effectiveness And Heat Transfer Distributions In Three Temperature Convection Situations" ASME paper 91-GT-345, Vedula et al. (Jun. 1991).

* cited by examiner

Primary Examiner—Diego Gutierrez
Assistant Examiner—Stanley J. Pruchnic, Jr.
(74) Attorney, Agent, or Firm—AFMCLO/JAZ; Richard A. Lambert

(57) ABSTRACT

A method of infrared thermography is described. The invention utilizes a high resolution infrared thermography system and associated computer in conjunction with a test chamber to determine heat transfer coefficients and film effectiveness values from a single test.

4 Claims, 2 Drawing Sheets

METHOD OF INFRARED THERMOGRAPHY

RIGHTS OF THE GOVERNMENT

The invention described herein may be manufactured and used by or for the Government of the United States for all governmental purposes without the payment of any royalty.

BACKGROUND OF THE INVENTION

The present invention relates generally to infrared thermography and more particularly to an infrared thermography method for determining film cooled heat transfer coefficients and film effectiveness from a single test.

Film cooling is used extensively in modern gas turbines to cool hot gas path components. Film cooling is effected by injecting a cooler fluid onto the hotter surface through holes or slots provided within the surface of the turbine blades or vanes. As high performance turbine engine technologies advance, turbine inlet temperatures are raised to higher and higher values to achieve higher thermal efficiency. These higher temperatures necessitate effective film cooling to protect the turbine components. A competing consideration for the turbine designer is the fact that diversion of pressurized air from the compressor section for cooling purposes decreases the overall efficiency of the engine. Thus, the designer carefully considers the effectiveness of film cooling to keep turbine engine efficiencies as high as possible. For example, the geometry of the cooling holes, incident angles, size, geometry and shape of the turbine blades, etc. are all considerations for the turbine engine designer to take into account in order to maximize cooling efficiency. Towards that end, knowledge of both the heat transfer coefficient and adiabatic wall temperature is necessary for the designer to predict and ascertain the benefits and the level of film cooling induced heat flux reduction, requiring that experimentation must be performed for each geometry under consideration in order to prove the efficacy of each. Such experimentation is costly, both in terms of expenditure of time and money and obviously, any reduction in these costs by improving testing techniques would be desirable.

In the past, the techniques for obtaining film cooled heat transfer coefficients and film effectiveness values traditionally required two different, related experiments wherein the values are obtained separately. Some of the techniques used low resolution methods such as thermocouples and heater foils, mass transfer analogy methods, etc. In the past decade, the most popular technique for obtaining high resolution measurements has been the liquid crystal technique. In this technique, the test article is painted with a coating of thermochromic liquid crystals prior to test. During the test, the crystals display different colors or hues in response to the temperatures encountered. The color change over the duration of the test is then utilized to indicate the temperature ranges encountered by the regions of interest on the test article and these temperature values are utilized to compute the film cooled heat transfer coefficients and film effectiveness values.

One such liquid crystal technique is described in "A method for the simultaneous determination of local effectiveness and heat transfer distributions in three-temperature convection situations" by Vedula and Metzger appearing in ASME paper 91-GT-345. Vedula and Metzger suggested a simultaneous measurement of film cooled heat transfer coefficients and film effectiveness values from a single test using the above described liquid crystal coating approach. This approach proved problematic, however, due to difficulties associated with obtaining both measurements from a single test in light of the relatively slow color change characteristics of the liquid crystals themselves.

In order to solve this problem, resort was made to two, related yet separate, tests to resolve the film cooled heat transfer coefficients and film effectiveness values at every point on the test surface. This two test method has enjoyed some measure of success but, the desirability of determining both values from a single test remains. Since then, several investigators have attempted various techniques to obtain both film cooled heat transfer coefficients and film effectiveness values but have been largely unsuccessful.

A need exists therefore for an improved method for determining film cooled heat transfer coefficients and film effectiveness values. Such a method would desirably enable the simultaneous determination of both values from a single test while avoiding the use of thermochromic liquid crystals for temperature determination and the attendant problems associated therewith.

SUMMARY OF THE INVENTION

Accordingly, it is a primary object of the present invention to provide a method for determining film cooled heat transfer coefficients and film effectiveness values overcoming the limitations and disadvantages of the prior art.

Another object of the present invention is to provide a method of infrared thermography for simultaneously determining film cooled heat transfer coefficients and film effectiveness values from a single test.

Yet another object of the present invention is to provide a method of infrared thermography for simultaneously determining film cooled heat transfer coefficients and film effectiveness values from a single test without the use of thermographic crystal techniques.

Additional objects, advantages and other novel features of the invention will be set forth, in part, in the description that follows and will, in part become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects and in accordance with the purposes of the present invention as described herein, the method of infrared thermography utilizes a high resolution infrared thermography system in conjunction with a computer for quickly performing a large number of iterative calculations to experimentally determine film cooled heat transfer coefficients and film effectiveness values of a film cooled component.

The method of the present invention advantageously utilizes a commercially available infrared thermography system for accurately providing a series of pixel by pixel surface temperature distribution images. A test chamber is provided having a selectively operable source of mainstream air flow, a mainstream air flow heater, a mainstream diverter valve, a selectively operable source of coolant flow and a corresponding coolant diverter valve. Due to the number of iterative calcuations involved, a computer is utilized in conjunction with the invention in order to derive the desired film cooled heat transfer coefficients and film effectiveness values. The infrared thermography system includes an infrared camera which is directed into a test chamber. As will be described in more detail below, the system is calibrated by painting the test article flat black in order to determine the emissivity of the surface. This emissivity value is utilized by the infrared thermography system in determining temperature. The test article, which is often an airfoil or its simulated model, is then placed in the test chamber.

In order to initiate the test, the mainstream heater is utilized to heat the mainstream air flow to an elevated value. The actual temperature value is not critical and is primarily chosen to provide a distinct differential over the coolant flow, which for the purpose of expediency is ambient temperature. For example, mainstream air flow temperatures in the range of 130° F. provide satisfactory results. As the mainstream air flow is being heated, the flow is diverted away from the test chamber. The source of coolant flow is initiated at the same time and is diverted as well. When the mainstream flow reaches the desired temperature, both flows are simultaneously directed into the test chamber by actuation of their respective diverter valves.

Utilizing the infrared thermography system in conjunction with the computer, a series of surface temperature distribution images are taken and stored. These images are a pixel by pixel representation of the temperatures experienced by the test article. The size of the image is chosen based on the area of interest of the test image and can be varied to maximize testing efficiency.

A first surface temperature distribution is determined at a time $t_1$ and a second surface temperature distribution is determined at a time $t_2$. The film cooled heat transfer coefficient ($h_f$) and film effectiveness ($\eta$) are then determined by simultaneously solving the following equations for each pixel.

1) $\dfrac{T_{w1} - T_i}{(1-\eta)T_m + \eta T_c - T_i} = 1 - \exp\left(\dfrac{h_f^2 \alpha t_1}{k^2}\right) erfc\left(\dfrac{h_f \sqrt{\alpha t_1}}{k}\right)$ and, 2) $\dfrac{T_{w2} - T_i}{(1-\eta)T_m + \eta T_c - T_i} = 1 - \exp\left(\dfrac{h_f^2 \alpha t_2}{k^2}\right) erfc\left(\dfrac{h_f \sqrt{\alpha t_2}}{k}\right)$ Advantageously, the method of infrared thermography of the present invention quickly and accurately provides film cooled heat transfer coefficient values and film effectiveness values from a single test. This enables the turbine designer to accurately predict the overall effectives of proposed film cooling elements. The method of the present invention avoids the expensive use of thermographic liquid crystals to provide temperature values. Additionally, by enabling the designer to determine film cooled heat transfer coefficient values and film effectiveness values from a single test, the inaccuracies and uncertainties arising from running two different tests at two different times are avoided. Avoidance of the liquid crystals also enables a broader range of testing because liquid crystals can't reliably operate beyond 50° C.

BRIEF DESCRIPTION OF THE DRAWING

The accompanying drawing incorporated in and forming a part of the specification, illustrates several aspects of the present invention and together with the description serves to explain the principles of the invention. In the drawing.

DETAILED DESCRIPTION OF THE INVENTION

Figure 1:
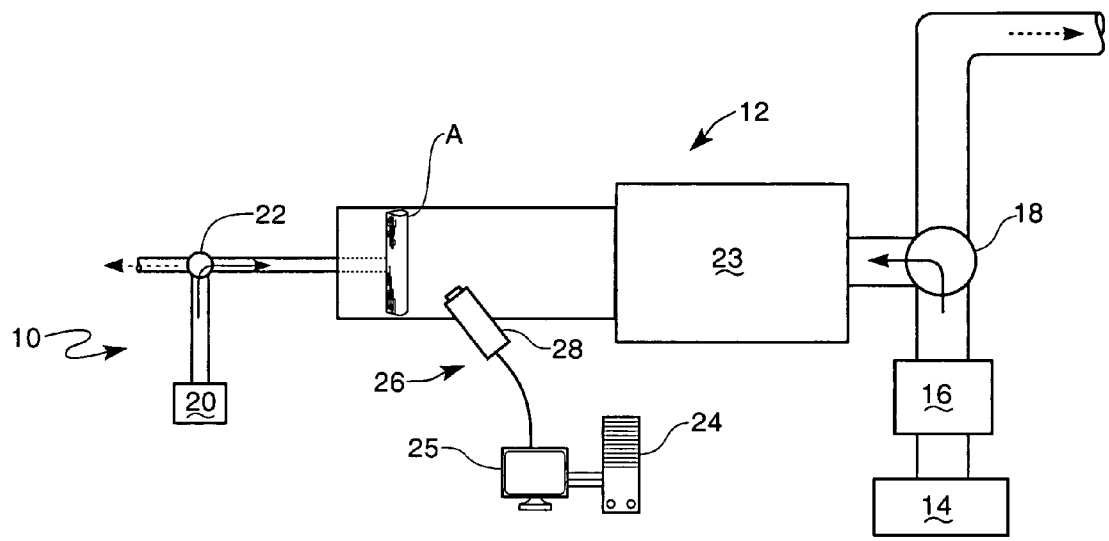
FIG. 1 is a diagrammatic representation of a test apparatus suitable for use with the method of the present invention.

In accordance with the present invention, a method of infrared thermography for simultaneously determining film cooled heat transfer coefficients and film effectiveness values from a single test is described. As shown in FIG. 1, a typical test system 10 suitable for performing the method of the present invention is presented.

Figure 2:
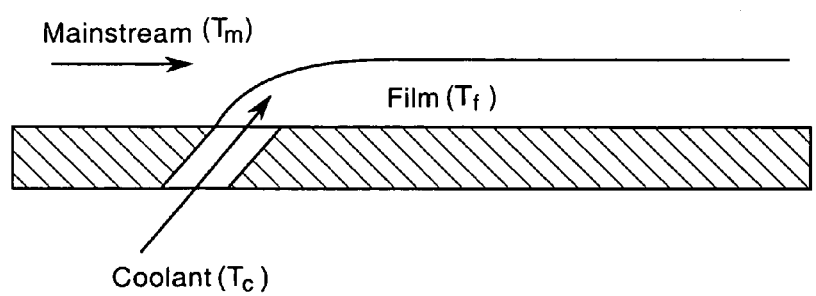
FIG. 2 is a diagrammatic representation of film cooling of an article.

FIG. 2 is a diagrammatic representation of typical film cooling hole situation. The mainstream is the air coming over the wall and the temperature of the flow is indicated as mainstream temperature ($T_m$). The coolant temperature ($T_c$) is the temperature before injection through the hole. After injection, the mainstream and coolant mix and produce the local film temperature ($T_f$). The film temperature $T_f$ is closer to coolant temperature immediately after the injection hole and then degrades as the coolant coverage decreases downstream and ultimately approaches the value of the mainstream temperature. Film effectiveness ($\eta$) is the non-dimensional temperature associated to the film temperature.

$$\eta = \dfrac{T_m - T_f}{T_m - T_c}$$

The heat transfer coefficient without film cooling (h) is the convective heat transfer coefficient defined from the heat flux equation:

$$q'' = h(T_m - T_w)$$

wherein q" is the heat flux without film cooling, $T_m$ is the mainstream temperature, and $T_w$ is the local surface temperature. The heat transfer coefficient is independent of the heat flux and temperature gradient and is a function of flow, fluid, and geometry. Similarly, the film cooled heat flux is defined as.

$$q''_f = h_f(T_f - T_w)$$

Accordingly, if the heat flux with film cooling is lower than the heat flux without film cooling, then the film cooling is demonstrated to reduce the heat transfer. It is very possible for a film cooling hole at a particular coolant flow rate to produce reasonable film effectiveness but much more significant rise in local heat transfer coefficient resulting in increase in heat flux.

As shown in FIG. 1, a test chamber 12 is provided having a selectively operable source of mainstream air flow 14 which can be an air pump, compressor or the like, a mainstream flow heater 16, a mainstream diverter valve 18, a selectively operable source of coolant flow 20, and a corresponding coolant diverter valve 22. The test chamber 12 additionally includes a settling chamber 23 for straightening the airflow to reduce turbulence. Due to the complexity and number of iterative calcuations necessary in performing the method of the present invention, a computer 24 is utilized in conjunction with the invention in order to derive the desired film cooled heat transfer coefficients and film effectiveness values. The computer can be any suitable system such as desktop or laptop personal computers or dedicated mainframe, and is a matter of choice for the practitioner. A monitor 25 is operatively connected to the computer 24 as well.

The test system 10 additionally includes a high resolution infrared thermography system 26 which includes an infrared camera 28 that is directed into the test chamber 12 and focused on the test article A. One infrared thermography system suitable for use in the method of the present invention is the FLIR systems ThermaCAM SC 3000, available from FLIR Systems AB, Danderyd, Sweden. Advantageously, use of infrared imaging techniques provides a high quality, non-intrusive method for obtaining thermal data. The infrared thermography system 26 can quickly identify transient temperature changes, unlike the thermochromic liquid crystal techniques relied upon by the methods of the prior art. The system 26 includes a software package for data analysis image creation and manipulation. The computer 24 is utilized to perform the method steps of the system's software as well as the data analysis calculations which will described in more detail below. The images and field of view of the infrared camera 28 can be viewed on the monitor 25.

In order to perform the method of the present method, the test system must first be calibrated. First, the surface of the test article A is painted flat black and reference thermocouples (not shown) are placed thereon and used to estimate the emissivity of the surface. The test article, thus prepared, is placed into the test chamber 12. The infrared camera 28 is focused on the test surface area of interest, which will typically be downstream of the cooling hole. The surface of the test article A is then heated using hot air from the blower. The thermocouples are monitored during the heat up and subsequent achievement of steady state. The temperature, determined by the infrared system 26 and the temperatures indicated by the thermocouples are compared to determine the emissivity. By way of example, the emissivity of the test article utilized during our experiments, when viewed through a calcium fluoride window was 0.96. Generally, emissivity values of flat black coated test surfaces would typically be in the range of 0.93–0.97.

Once the initial calibration operation has been completed, the system is ready for further use in testing operations. In order to initiate the test, the mainstream flow from the source 14 is heated by the mainstream heater 16 and diverted away from the test chamber 12 (see the dotted action arrow). It has been determined that mainstream air flow temperatures in the range of 130° F. provide satisfactory results. It should be pointed out, however, that the actual temperature value is not critical and is primarily chosen to provide a distinct differential over the coolant flow temperature, which for the purpose of expediency is ambient temperature. The coolant flow is initiated from the source 20 and is also routed away from the test section (see respective dotted action arrow). Once the mainstream flow reaches the required temperature, the mainstream diverter valve 18 and the coolant diverter valve 22 are simultaneously actuated in order to deliver the mainstream flow into the test chamber and the coolant flow into the test article A simultaneously. The infrared camera 28 is initiated to take images at the same instant.

Utilizing the infrared thermography system 26 in conjunction with the computer 24, a series of surface temperature distribution images are taken and stored. The size of the image is chosen based on the area of interest of the test article A and can be varied to maximize testing efficiency. These images are a pixel by pixel representation of the temperatures experienced by the test article A. An initial temperature distribution $T_i$ is taken at an initial image at a time $t_0$. A first surface temperature distribution $T_{w1}$, is determined at a time $t_1$ and a second surface temperature distribution $T_{w2}$, is determined at a time $t_2$.

Figure 3:
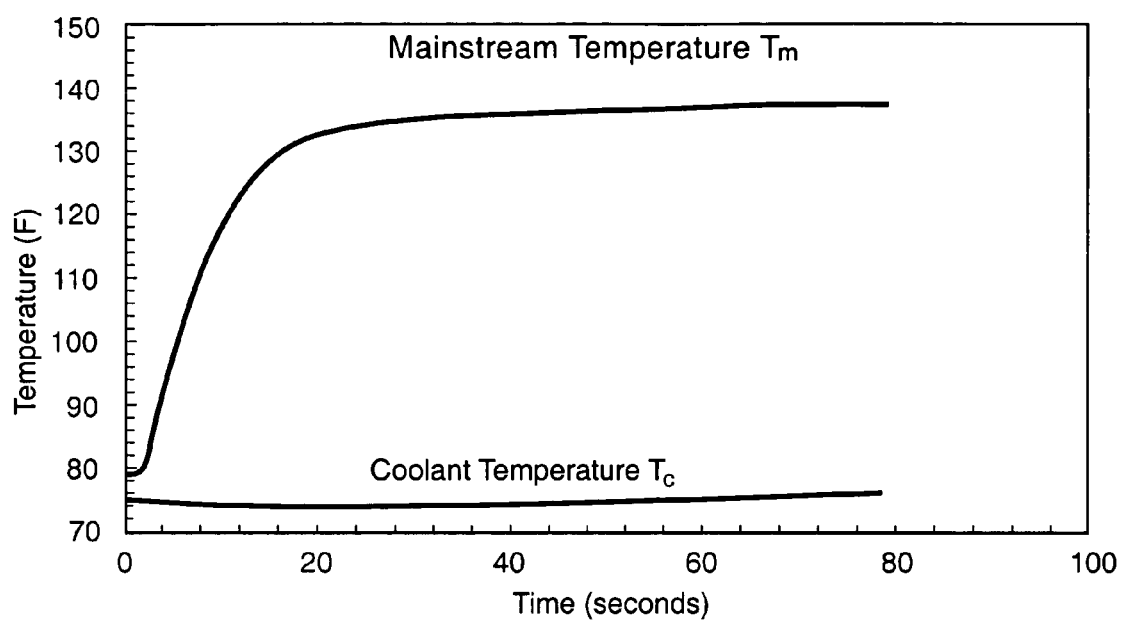
FIG. 3 is a graph depicting typical test conditions.

Reference is made to FIG. 3. The mainstream temperature $T_m$ within the test chamber as determined by a thermocouple (not shown), rises rather quickly from ambient to reach the heated temperature as described above. The coolant temperature determined by a thermocouple inside the test article adjacent to the film hole (not shown) is, however, maintained at ambient temperature. In order to assure an accurate test, the time $t_1$ for determining the first temperature distribution $T_{w1}$ is chosen to fall within the temperature rise portion of the curve, which during our tests was between about 15–20 seconds. The time $t_2$ for determining the second temperature distribution $T_{w2}$ is chosen to fall within the more level portion of the curve, which during our tests was chosen within the range of about 60–70 seconds. The choice of times $t_1$ and $t_2$ was made to provide a suitable differential to assure accurate test results and can be varied in order to suit local testing conditions.

The film cooled heat transfer coefficient($h_f$) and film effectiveness ($\eta$) are then determined by simultaneously solving the following equations for each pixel within the temperature distributions:

$$1) \quad \frac{T_{w1} - T_i}{(1-\eta)T_m + \eta T_c - T_i} = 1 - \exp\left(\frac{h_f^2 \alpha t_1}{k^2}\right) erfc\left(\frac{h_f \sqrt{\alpha t_1}}{k}\right) \text{ and,}$$

$$2) \quad \frac{T_{w2} - T_i}{(1-\eta)T_m + \eta T_c - T_i} = 1 - \exp\left(\frac{h_f^2 \alpha t_2}{k^2}\right) erfc\left(\frac{h_f \sqrt{\alpha t_2}}{k}\right)$$

wherein $T_{w1}$ and $T_{w2}$ are pixel surface temperature values from the respective $T_{w1}$ and $T_{w2}$ surface temperature distributions, $T_m$ is the mainstream temperature, $T_c$ is the coolant temperature, $T_i$ is the initial temperature from the image at $t_0$, $\alpha$ is thermal diffusivity, k is thermal conductivity.

In summary, numerous benefits have been described from utilizing the principles of the present invention. The method of infrared thermography utilizes a high resolution infrared thermography system and associated computer in conjunction with a test chamber to provide for the efficient determination of heat transfer coefficient values and film effectiveness values from a single test, overcoming the limitations and disadvantages of the two test methods of the prior art.

The foregoing description of the preferred embodiment has been presented for purposes of illustration and description. It is not intended to be exhaustive or to limit the invention to the precise form disclosed. Obvious modifications or variations are possible in light of the above teachings. The embodiment described was chosen to provide the best illustration of the principles of the invention and its practical application to thereby enable one of ordinary skill in the art to utilize the inventions in various embodiments and with various modifications as are suited to the particular scope of the invention as determined by the appended claims when interpreted in accordance with the breadth to which they are fairly, legally and equitably entitled.

The invention claimed is:

1. A method for determining film cooled heat transfer coefficients and film effectiveness values from a single test, comprising the steps of:
   providing a high resolution infrared thermography system having an infrared camera;
   providing a test article;
   providing a test chamber having a selectively operable source of mainstream flow, a mainstream heater, a mainstream diverter valve for selectively diverting the mainstream flow either into or away from said test chamber, a selectively operable source of coolant flow, and a coolant diverter valve for selectively diverting the coolant flow either into or away from said test article;
providing a mainstream thermocouple and a coolant thermocouple;
installing said test article within said test chamber;
calibrating said infrared thermography system;
initiating a mainstream flow from said source of mainstream flow and heating said mainstream flow to a preselected temperature while diverting said mainstream flow away from said test chamber;
initiating a coolant flow from said source of coolant flow while diverting said coolant flow away from said test article;
simultaneously actuating said mainstream diverter valve and said coolant diverter valves to direct said coolant flow into said test article and said mainstream flow into said test chamber;
creating a series of surface temperature distribution images, through use of said infrared thermography system, by acquiring a series of infrared images upon enactment of said actuating step above, digitizing each pixel of said infrared image and converting each said pixel to a corresponding temperature value;
recording a series of mainstream and coolant temperatures through the use of said thermocouples;
obtaining, from said creating step above, an initial temperature distribution, $T_i$, from an initial test image at a time $t_0$;
obtaining, from said creating step above, a first surface temperature distribution, $T_{w1}$, from a test image at a time $t_1$;
obtaining, from said creating step above, a second surface temperature distribution, $T_{w2}$, from a test image at a time $t_2$;
determining, at each pixel, the film cooled heat transfer coefficient ($h_f$) and film effectiveness ($\eta$) by simultaneously solving the following equations:

$$1)\ \frac{T_{w1} - T_i}{(1-\eta)T_m + \eta T_c - T_i} = 1 - \exp\left(\frac{h_f^2 \alpha t_1}{k^2}\right) erfc\left(\frac{h_f \sqrt{\alpha t_1}}{k}\right) \text{ and,}$$

$$2)\ \frac{T_{w2} - T_i}{(1-\eta)T_m + \eta T_c - T_i} = 1 - \exp\left(\frac{h_f^2 \alpha t_2}{k^2}\right) erfc\left(\frac{h_f \sqrt{\alpha t_2}}{k}\right)$$

wherein $T_{w1}$ and $T_{w2}$ are pixel surface temperature values at said times $t_1$ and $t_2$ from said $t_1$ and $t_2$ obtaining steps respectively, and wherein the two unknowns are film cooled heat transfer coefficient ($h_f$) and film effectiveness ($\eta$) and wherein the initial temperature $T_i$ for each corresponding pixel point is obtained from said initial temperature distribution, $T_i$, from said $t_0$ obtaining step above, $T_m$ and $T_c$ are mainstream and coolant temperatures obtained by said thermocouples, and wherein $\alpha$ is thermal diffusivity, and k is thermal conductivity.

2. The method of claim 1 wherein said mainstream thermocouple is within said test chamber.

3. The method of claim 1 wherein said coolant thermocouple is within said test article.

4. A method for determining film cooled heat transfer coefficients and film effectiveness values from a single test, comprising the steps of:
providing a high resolution infrared thermography system having an infrared camera;
providing a test article;
providing a coolant thermocouple within said test article;
providing a test chamber having a selectively operable source of mainstream flow, a mainstream heater, a mainstream diverter valve for selectively diverting the mainstream flow either into or away from said test chamber, a selectively operable source of coolant flow, and a coolant diverter valve for selectively diverting the coolant flow either into or away from said test article;
providing a mainstream thermocouple within said test chamber;
installing said test article within said test chamber;
calibrating said infrared thermography system;
initiating a mainstream flow from said source of mainstream flow and heating said mainstream flow to a preselected temperature while diverting said mainstream flow away from said test chamber;
initiating a coolant flow from said source of coolant flow while diverting said coolant flow away from said test article;
simultaneously actuating said mainstream diverter valve and said coolant diverter valves to direct said coolant flow into said test article and said mainstream flow into said test chamber;
creating a series of surface temperature distribution images, through use of said infrared thermography system, by acquiring a series of infrared images upon enactment of said actuating step above, digitizing each pixel of said infrared image and converting each said pixel to a corresponding temperature value;
recording a series of mainstream and coolant temperatures through the use of said thermocouples;
obtaining, from said creating step above, an initial temperature distribution, $T_i$, from an initial test image at a time $t_0$;
obtaining, from said creating step above, a first surface temperature distribution, $T_{w1}$, from a test image at a time $t_1$;
obtaining, from said creating step above, a second surface temperature distribution, $T_{w2}$, from a test image at a time $t_2$;
determining, at each pixel, the film cooled heat transfer coefficient ($h_f$) and film effectiveness ($\eta$) by simultaneously solving the following equations:

$$1)\ \frac{T_{w1} - T_i}{(1-\eta)T_m + \eta T_c - T_i} = 1 - \exp\left(\frac{h_f^2 \alpha t_1}{k^2}\right) erfc\left(\frac{h_f \sqrt{\alpha t_1}}{k}\right) \text{ and,}$$

$$2)\ \frac{T_{w2} - T_i}{(1-\eta)T_m + \eta T_c - T_i} = 1 - \exp\left(\frac{h_f^2 \alpha t_2}{k^2}\right) erfc\left(\frac{h_f \sqrt{\alpha t_2}}{k}\right)$$

wherein $T_{w1}$ and $T_{w2}$ are pixel surface temperature values at said times $t_1$ and $t_2$ from said $t_1$ and $t_2$ obtaining steps respectively, and wherein the two unknowns are film cooled heat transfer coefficient ($h_f$) and film effectiveness ($\eta$) and wherein the initial temperature $T_i$ for each corresponding pixel point is obtained from said initial temperature distribution, $T_i$, from said $t_0$ obtaining step above, $T_m$ and $T_c$ are mainstream and coolant temperatures obtained by said thermocouples, and wherein $\alpha$ is thermal diffusivity, and k is thermal conductivity.

* * * * *